(12) United States Patent
Nabutovsky et al.

(10) Patent No.: US 7,920,913 B1
(45) Date of Patent: Apr. 5, 2011

(54) SYSTEMS AND METHODS FOR INCREASING IMPLANTABLE SENSOR ACCURACY

(75) Inventors: Yelena Nabutovsky, Mountain View, CA (US); Gene A. Bornzin, Simi Valley, CA (US); Kyungmoo Ryu, Palmdale, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 906 days.

(21) Appl. No.: 11/771,514

(22) Filed: Jun. 29, 2007

(51) Int. Cl.
*A61B 5/04* (2006.01)

(52) U.S. Cl. ...................................................... 600/509

(58) Field of Classification Search .................. 600/511
See application file for complete search history.

(56) References Cited

U.S. PATENT DOCUMENTS

| | | |
|---|---|---|
| 3,939,824 A | 2/1976 | Arneson |
| 4,036,217 A | 7/1977 | Ito |
| 4,137,907 A | 2/1979 | Jansen |
| 4,190,886 A | 2/1980 | Sherman |
| 4,223,681 A | 9/1980 | Sherman |
| 4,305,398 A | 12/1981 | Sawa |
| 4,461,266 A | 7/1984 | Hood |
| 4,505,276 A | 3/1985 | Markowitz et al. |
| 4,700,708 A | 10/1987 | New |
| 4,759,369 A | 7/1988 | Taylor |
| 4,815,469 A | 3/1989 | Cohen et al. |
| 4,869,254 A | 9/1989 | Stone et al. |
| 4,919,144 A | 4/1990 | Vandehey |
| 5,078,136 A | 1/1992 | Stone et al. |
| 5,129,392 A | 7/1992 | Bardy |
| 5,241,964 A | 9/1993 | McQuilkin |
| 5,309,916 A | 5/1994 | Hatschek |
| 5,343,868 A | 9/1994 | Kurscheidt |
| 5,533,511 A | 7/1996 | Kaspari |
| 5,797,399 A | 8/1998 | Morris |
| 5,957,861 A | 9/1999 | Combs |
| 6,122,536 A | 9/2000 | Sun et al. |

(Continued)

FOREIGN PATENT DOCUMENTS

EP 1302156 A2 4/2003

(Continued)

OTHER PUBLICATIONS

Non-Final Office Action mailed May 4, 2007: Related U.S. Appl. No. 10/897,336.
Notice of Allowance mailed Oct. 5, 2007: Related U.S. Appl. No. 10/897,336.
Non-Final Office Action mailed Jan. 10, 2006: Related U.S. Appl. No. 10/895,165.
Final Office Action mailed May 25, 2006: Related U.S. Appl. No. 10/895,165.

(Continued)

*Primary Examiner* — Carl H Layno
*Assistant Examiner* — Paula J Stice
(74) *Attorney, Agent, or Firm* — Steven M. Mitchell

(57) ABSTRACT

Provided herein are implantable systems, and methods for use therewith, that increase the accuracy of measurements produced using an implanted sensor, where the measurements are affected by cycles of a cyclical body function (e.g., heart beat and/or respiration). In accordance with specific embodiments of system, a measurement that is presumed to be accurate is obtained. The measurement can be of a physiologic property, such as, but not limited to, blood oxygen saturation, hematocrit, or blood glucose concentration. Additionally, the implanted is used to produce a plurality of measurements of the physiologic property. Such measurements, produced using the implanted sensor, are compared to the measurement presumed to be accurate to thereby identify when the measurements produced using the implanted sensor are most accurate. Thereafter, the implanted system is configured to use the implanted sensor to produce measurements when the measurements produced using the implanted sensor are most accurate.

29 Claims, 6 Drawing Sheets

U.S. PATENT DOCUMENTS

| | | |
|---|---|---|
| 6,409,675 B1 | 6/2002 | Turcott |
| 6,480,733 B1 | 11/2002 | Turcott |
| 6,512,949 B1 * | 1/2003 | Combs et al. ............... 600/547 |
| 6,519,486 B1 | 2/2003 | Edgar |
| 6,561,984 B1 | 5/2003 | Turcott |
| 6,575,912 B1 | 6/2003 | Turcott |
| 6,591,131 B2 | 7/2003 | Dal-Molin |
| 7,092,759 B2 | 8/2006 | Nehls et al. |
| 2001/0034488 A1 | 10/2001 | Policker |
| 2004/0042581 A1 | 3/2004 | Okerlund |
| 2004/0077953 A1 | 4/2004 | Turcott |
| 2004/0254483 A1 | 12/2004 | Zdeblick et al. |
| 2005/0137487 A1 | 6/2005 | Zhu |

FOREIGN PATENT DOCUMENTS

| | | | |
|---|---|---|---|
| WO | 9701986 A1 | 1/1997 | |

OTHER PUBLICATIONS

Advisory Action mailed Aug. 2, 2006: Related U.S. Appl. No. 10/895,165.

Non-Final Office Action mailed Sep. 29, 2006: Related U.S. Appl. No. 10/895,165.

Non-Final Office Action mailed Feb. 25, 2008: Related U.S. Appl. No. 10/894,962.

Non-Final Office Action mailed Sep. 16, 2008: Related U.S. Appl. No. 10/894,962.

Final Office Action mailed Aug. 4, 2009: Related U.S. Appl. No. 10/894,962.

Non-Final Office Action mailed Oct. 16, 2006: Related U.S. Appl. No. 10/895,004.

* cited by examiner

SYSTEMS AND METHODS FOR INCREASING IMPLANTABLE SENSOR ACCURACY

CROSS-REFERENCE TO RELATED APPLICATIONS

The present application relates to the following commonly assigned patent applications, each of which were filed on Jul. 19, 2004, each of which name Robert Turcott as the inventor, and each of which is incorporated herein by reference:

U.S. patent application Ser. No. 10/897,336 entitled "Reducing Data Acquisition, Power and Processing for Photoplethysmography and Other Applications";

U.S. patent application Ser. No. 10/895,165 entitled "Reducing Data Acquisition, Power and Processing for Hemodynamic Signal Amplitude Detection";

U.S. patent application Ser. No. 10/894,962 entitled "Reducing Data Acquisition, Power and Processing for Hemodynamic Signal Sampling"; and U.S. patent application Ser. No. 10/895,004 entitled "Reducing Data Acquisition, Power and Processing for Pulse Oximetry Applications".

FIELD OF THE INVENTION

Embodiments of present invention relate to the use of implantable sensors, such as, but not limited to oxygen saturation sensors, which can be sensitive to changes in cyclical body functions, such as respiration and heart beat.

BACKGROUND

Some implantable sensors are sensitive to changes that take place within a cardiac and/or respiratory cycle. An example of such an implantable sensor is a venous oxygen saturation sensor (SvO2), which can be placed, e.g., inside a blood vessel or a chamber of a heart. An SvO2 sensor includes light sources to transmit light of multiple wavelengths. The transmitted light interacts with surrounding blood, and is either absorbed or reflected back and detected by one or more light detector of the SvO2 sensor. The portions of the light absorbed and reflected depend on the oxygen level of the blood. Thus, the levels of the light detected by the light detector(s) can be used to measure venous oxygen saturation levels. However, other factors can also affect how much light is absorbed and reflected. For example, the placement of the sensor can have a strong effect on how light is absorbed and reflected. More specifically, if the light sources face a vessel wall or chamber wall, the amount of reflected light might be greatly increased during heart contractions because light would reflect off of the vessel or chamber wall without interacting with the blood. In this case, the measurements made during contractions would likely be inaccurate. Direction of blood flow and cell orientation relative to the sensor can also influence sensor measurements by changing the balance between reflection and absorption. For another example, movement of the chest wall, due to respiration, can also alter sensor measurements.

Sensor measurements can be used in various manners, such as, for feedback when adjusting pacing parameters, for monitoring heart failure patients, for triggering therapy and/or alarms, etc. From the above description, it is clear that various factors can affect the accuracy of sensor measurements. It would be undesirable and potentially detrimental to use such inaccurate sensor measurements for feedback, monitoring, triggering therapy and/or alarms, or the like. Accordingly, there is a need to increase the accuracy of sensor measurements obtained from implantable sensors.

SUMMARY

Embodiments of the present invention are directed to implantable systems, and methods for use therewith, that increase the accuracy of measurements produced using an implanted sensor, where the measurements are affected by cycles of a cyclical body function.

In accordance with specific embodiments of the present invention, a measurement that is presumed to be accurate is obtained. The measurement can be of a physiologic property, such as, but not limited to, blood oxygen saturation, hematocrit, blood glucose concentration, or the like. Additionally, an implanted sensor is used to produce a plurality of measurements of the physiologic property. Such measurements, produced using the implanted sensor, are compared to the measurement presumed to be accurate to thereby identify when the measurements produced using the implanted sensor are most accurate. Thereafter, the implanted system is configured to use the implanted sensor to produce measurements when the measurements produced using the implanted sensor are most accurate.

In specific embodiments, measurements produced using the implanted sensor are compared to the measurement presumed to be accurate to thereby identify a portion of cycles of the cyclical body function when the measurements produced using the implanted sensor are most accurate. Thereafter, the implanted system is configured to use the implanted sensor to produce measurements during the identified portion of cycles of the cyclical body function.

In specific embodiments, a sensor signal is obtained from the implanted sensor, and a plurality of measurements are determined based on the sensor signal. The measurements based on the sensor signal are compared to the measurement presumed to be accurate to thereby identify a portion of cycles of the cyclical body function when the measurements based on the sensor signal are most accurate. Thereafter, the implanted system is configured to produce measurements based on a portion of the sensor signal that corresponds to the identified portion of cycles of the cyclical body function.

The cyclical body function that affects sensor measurements can be heart beat, and the cycles of the cyclical body function can be cardiac cycles. Accordingly, specific embodiments include identifying the portion of cardiac cycles, when the measurements based on the sensor signal are most accurate, relative to a detectable cardiac event. The detectable cardiac event may be detected from a signal representative of cardiac activity, i.e., an intracardiac electrogram (EGM) or an electrocardiogram (ECG), obtained from implanted electrodes. More specifically, there can be an identification of a time interval after detected R-waves, P-waves, or any other EGM or ECG feature, when measurements based on a sensor signal are most accurate. Alternatively, there can be an identification of at what percentage of cyclical cardiac intervals (e.g., R-R or P-P intervals) the measurements based on a sensor signal are most accurate. In other embodiments, this can include identifying a portion of cardiac cycles, when the measurements produced using the implanted sensor are most accurate, relative to a detectable feature of the sensor signal (produced by the implanted sensor) itself. This is especially useful where a separate EGM is not available.

The cyclical function that affects sensor measurements can alternatively, or additionally, be respiration, and the cycles of the cyclical body function can be respiratory cycles. In specific embodiments, the portion of respiratory cycles, when the measurements based on the sensor signal are most accurate, is identified relative to a detectable respiratory event (e.g., inhalation or exhalation). In other embodiments, the portion of respiratory cycles, when the measurements based on the sensor signal are most accurate, is identified relative to a detectable feature of a low pass filtered version of the sensor signal. This is especially useful where a separate respiratory signal is not available.

It is also possible that a sensor signal is affected by both cardiac cycles of heart beat and respiratory cycles of respiration. Accordingly, specific embodiments include identifying when the measurements based on the sensor signal are most accurate relative to both detectable cardiac and respiratory events.

In specific embodiments, measurements can be obtained using the implanted sensor for a plurality of different cycle rates (e.g., heart rates and/or respiration rates). There can be the identification of the portion of a cycle of the cyclical body function when the measurements based on the sensor signal are most accurate for the all various cycle rates. Thereafter, the implanted system can be configured to produce measurements based on the sensor signal during the identified portion of cycles of the cyclical body function, wherein the identified portion of the cycles is the same for the various cycle rates.

Alternative embodiments includes identifying, for each of the different cycle rates, the portion of a cycle of the cyclical body function when the measurements based on the sensor signal are most accurate. Thereafter, the implanted system can be configured to produce measurements based on the sensor signal during the identified portion of cycles of the cyclical body function, wherein the identified portion of the cycles is dependent upon the cycle rate.

To further improve the accuracy of an implanted sensor, an offset between the measurements determined using the implanted sensor and the measurement presumed to be accurate can be determined. The implanted system can then be configured to use the determined offset to adjust measurements produced using the implanted sensor. As mentioned above, such measurements can be produced during the identified portion of the cycle of the cyclical body function, when the measurements are most accurate.

This description is not intended to be a complete description of, or limit the scope of, the invention. Other features, aspects, and objects of the invention can be obtained from a review of the specification, the figures, and the claims.

DETAILED DESCRIPTION

Figure 1A:
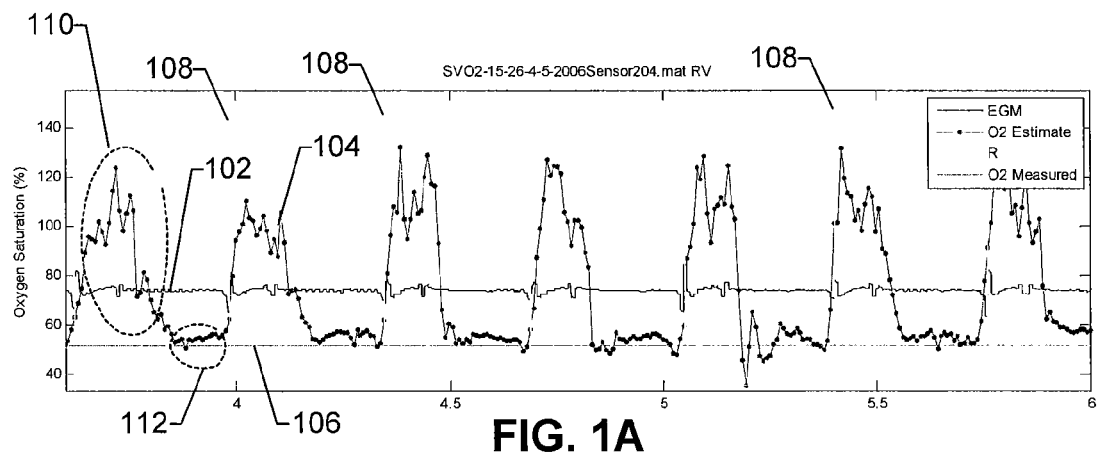
FIG. 1A is a graph that shows an EGM waveform, a waveform indicative of measurements of venous oxygen saturation produced using an implanted optical sensor and a waveform indicative of an accurate measurement of venous oxygen saturation, where the measurements produced using the implanted optical sensor are affected by cardiac cycles.

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit(s) of a reference number identifies the drawing in which the reference number first appears.

As explained above, the placement of implantable sensors, and the movement of the patient tissue and the like relative to such sensors, can affect measurements that are made using such sensors. It is typically difficult to control the exact placement of sensors at times of implant due to variation in patients' anatomy, additional lead placements, and other factors. Thus, it is not always possible to predict when in cardiac and respiratory cycles implantable sensors should be used to produce measurements. Specific embodiments of the present invention, described below, overcome this problem.

Embodiments of the present invention are especially useful for improving the accuracy of implanted optical sensors, such as implanted optical SvO2 sensors (also known as implanted oxygen saturation sensors). An exemplary implanted oxygen saturation sensor emits light of two or more wavelengths (e.g., from two or more LEDs) into a blood vessel or heart chamber, and detects reflected light. For estimating oxygen saturation, at least one of the LEDs' primary wavelength is chosen at some point in the electromagnetic spectrum where the absorption of oxyhemoglobin (HbO2) differs from the absorption of reduced hemoglobin (Hb). The one or more other wavelengths should be at a different point in the spectrum where, additionally, the absorption differences between Hb and HbO2 are different from those at the first wavelength. Oxygen saturation sensors typically utilize one wavelength in the red part of the visible spectrum near 660 nanometers (nm), and at least one in the near infrared part of the spectrum in the range of 880 nm-940 nm. Photocurrents generated within the photodetector are detected and processed for measuring the ratio of the red to infrared signals. This ratio has been observed to correlate well to oxygen saturation. It is also possible that a single wavelength is used, to not determine a ratio, but rather to measure relative changes in oxygen saturation. The sensor signal associated with such a sensor can be a signal that is indicative of measurements of block oxygen saturation. Such a sensor signal can be output by the implanted sensor, or a signal produced by a microcontroller or processor that processes raw output signals of the implanted sensor.

In addition to producing measures of blood oxygen saturation, implanted optical sensors can also be used to measure levels of hematocrit, which refers to the percentage of packed red blood cells in a volume of whole blood. Various techniques are known for determining hematocrit based on scattered light. In one technique, a pair of spatially separated photo detectors can be used to detect reflected infra red (IR) light, e.g., of 805 nm. The intensity of the IR light detected by the photo detector that is nearer to the IR light source is referred to as IRnear, and the intensity of the IR light detected by the photo detector farther from the IR light source is referred to as IRfar. As described in article by Bornzin et al., entitled "Measuring Oxygen Saturation and Hematocrit Using a Fiberoptic Catheter", *IEEE/9th Annual Conf of the Eng. & Biol. Soc.* (1997), which is incorporated herein by reference, the ratio: R=IRnear/IRfar is directly related to the level of hematocrit, but independent of oxygen saturation because 805 nm is an isobestic wavelength. Hematocrit can be measured with similar results using a single light detector, and two light sources, where one source is located closer to the light detector than the other (again producing IRnear and IRfar measurements). In another technique, light of about 500 nm and light of about 800 nm can be directed at a blood sample, and an algorithm can be used to calculate hematocrit based on the intensities of detected scattered light.

When an optical oxygen saturation sensor is chronically implanted, the light source and light detector can be within or attached to a lead that is attached to an implanted housing of a cardiac stimulation device. Such a lead can be implanted in a cardiac chamber, or in a blood vessel. It is also possible that the oxygen saturation sensor not be connected directly to a cardiac stimulation device housing. In such embodiments, the implanted oxygen saturation sensor may be autonomous and may include its own battery, memory, and microprocessor, and it may be in wireless communication with an implanted cardiac stimulation device or an external device that would trigger the implanted oxygen sensor to collect oxygen saturation data.

Additional exemplary details of how oxygen saturation levels and/or hematocrit levels can be produced based on a sensor signal from an implanted optical sensor are provided in the Related References listed and incorporated by reference above, as well as in the following commonly assigned applications, each of which are incorporated herein by reference: U.S. patent application Ser. No. 11/282,198, entitled "Implantable Self-Calibrating Optical Sensors," filed Nov. 17, 2005; and U.S. patent application Ser. No. 11/231,555, entitled "Implantable Multi-Wavelength Oximeter Sensor," filed Sep. 20, 2005.

Other exemplary sensors, with which embodiments of the present invention can be used, include, but are not limited to, impedance sensors, pressure sensors, other protein sensors, and the like. These are just a few exemplary implantable sensors that may produce a sensor signal that is affected by cycles of a cyclical body function. Embodiments of the present invention can also be used with other sensors that measure physiologic properties other than those mentioned above.

Figure 1B:
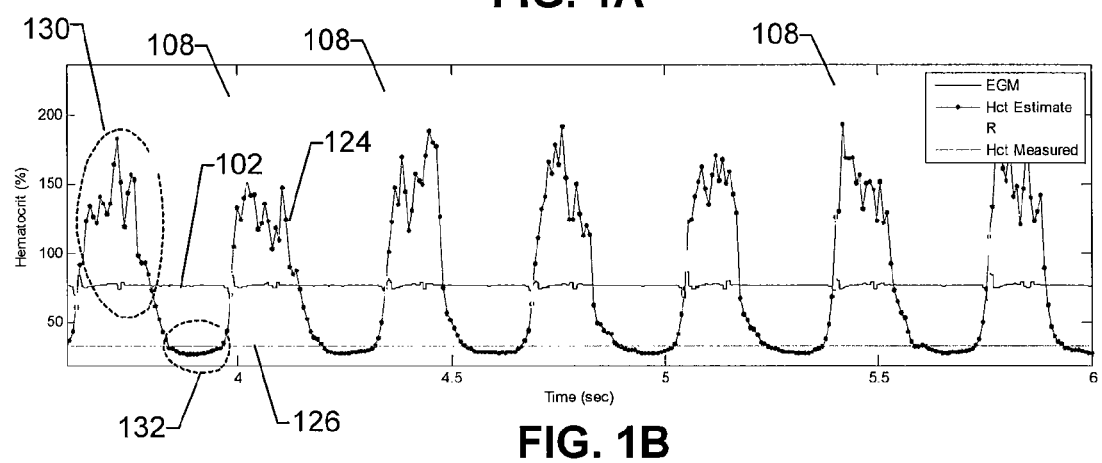
FIG. 1B is a graph that shows an EGM waveform, a waveform indicative of measurements of hematocrit produced using an implanted optical sensor and a waveform indicative of an accurate measurement of hematocrit, where the measurements produced using the implanted optical sensor are affected by cardiac cycles.

FIGS. 1A and 1B illustrate how a signal from an optical sensor, used to produce measures of venous oxygen saturation (SvO2) and hematocrit, can change greatly within each cardiac cycle. Referring to FIG. 1A, three waveforms are shown, including an electrogram (EGM) waveform 102, a waveform 104 indicative of measurements of venous oxygen saturation produced using an implanted optical sensor, and a waveform 106 indicative of an accurate (also referred to as "gold standard") measurement of venous oxygen saturation obtained, e.g., from a blood sample using a hemoximeter, or the like. In FIG. 1A, the vertical lines 108 are markers of R-wave peaks of the EGM 102. In this case, the implanted optical sensor is facing a heart wall. During heart contraction (systole), the wall approaches the sensor and light is reflected back into the photodetector of the sensor without properly interacting with the blood. This results in SvO2 measurements 110 (also referred to as estimates) that are inaccurate, and more specifically, much greater than the actual SvO2 value 106. In contrast, during heart relaxation (diastole), the heart wall moves farther away from the sensor, allowing it to fully interact with the blood. This results in SvO2 measurements 112 that are very close to the actual SvO2 value 106.

FIG. 1B is a similar graph but with a waveform 124 indicative of hematocrit measurements produced using an implanted optical sensor, and a waveform 126 indicative of an accurate (also referred to as "gold standard") measurement of hematocrit obtained, e.g., from a blood sample using a hematocrit centrifuge, or the like. Again, the waveform 102 is an EGM waveform and the vertical lines 108 are markers of R-wave peaks of the EGM 102. For similar reasons as discussed above with reference to FIG. 1A, during systole, the hematocrit measurements 130 (also referred to as estimates) are much greater than the actual hematocrit value 126; and during diastole, the hematocrit measurements 132 are very close to the actual hematocrit value 126.

As can be appreciated from FIGS. 1A and 1B, in these cases the SvO2 and hematocrit measurements obtained using an implanted optical sensor are most accurate during the second half of a cardiac cycle, i.e., during the latter portion of an R-R interval. While this is the case here, this can be different if the implanted sensor is implanted in a different location and/or in a different orientation.

Figure 2A:
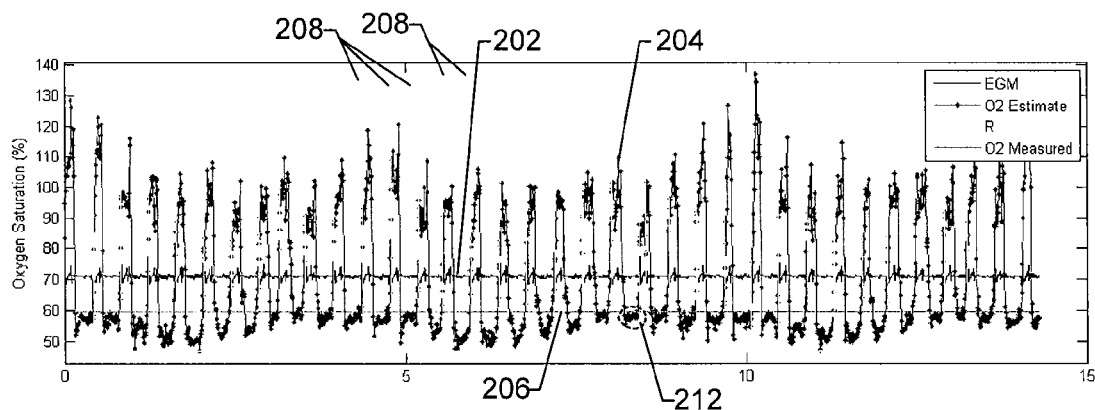
FIG. 2A is a graph similar to FIG. 1A, which shows the measurements of venous oxygen saturation produced using the implanted optical sensor also affected by respiratory cycles.
Figure 2B:
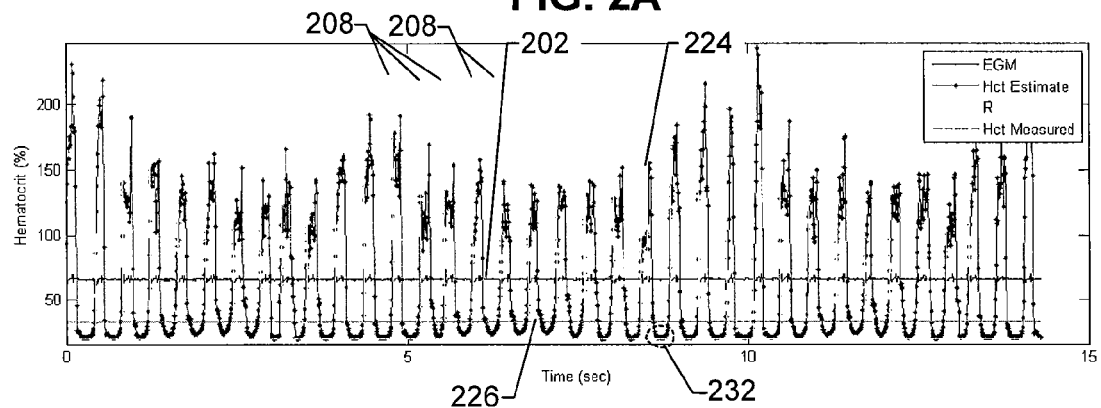
FIG. 2B is a graph similar to FIG. 1B, which shows the measurements of hematocrit produced using the implanted optical sensor also affected by respiratory cycles.

FIGS. 2A and 2B are similar to FIGS. 1A and 1B, but show a longer period of time, which enables the effects of respiratory cycles on the accuracy of measurements to also be revealed. Referring to FIG. 2A, shown are an EGM waveform 202, a waveform 204 indicative of measurements of venous oxygen saturation produced using the implanted optical sensor, and a waveform 206 indicative of an accurate measurement of venous oxygen saturation. In FIG. 2A, the vertical lines 208 are markers of R-wave peaks of the EGM 202. Here, the measurements (also referred to as estimates) obtained using the implanted optical sensor are shown as varying with both cardiac cycles and respiratory cycles. With each breath, the measurements of SvO2 obtained using the implanted optical sensor approach and subsequently deviate from the gold standard (i.e., accurate) measured value 206. From FIG. 2A, it appears that estimates of SvO2 are most accurate during peaks in respiration (indicative of inhalation) that correlate with diastole of a cardiac cycle, as indicated, e.g., at 212.

FIG. 2B is a similar plot with waveform 224 indicative of hematocrit measurements produced using the optical sensor, and waveform 226 indicative of an accurate (also referred to as "gold standard") measurement of hematocrit. Again, the waveform 202 is an EGM waveform and the vertical lines 208 are markers of R-wave peaks of the EGM 202. Similarly, with each breath, the measurements (also referred to as estimates) of hematocrit obtained using the implanted optical sensor approach and subsequently deviate from the gold standard (i.e., accurate) measured value 226. From FIG. 2B, it appears that estimates of hematocrit are most accurate during peaks in respiration (indicative of inhalation) that correlate with diastole of a cardiac cycle, as indicated, e.g., at 232.

Figure 3A:
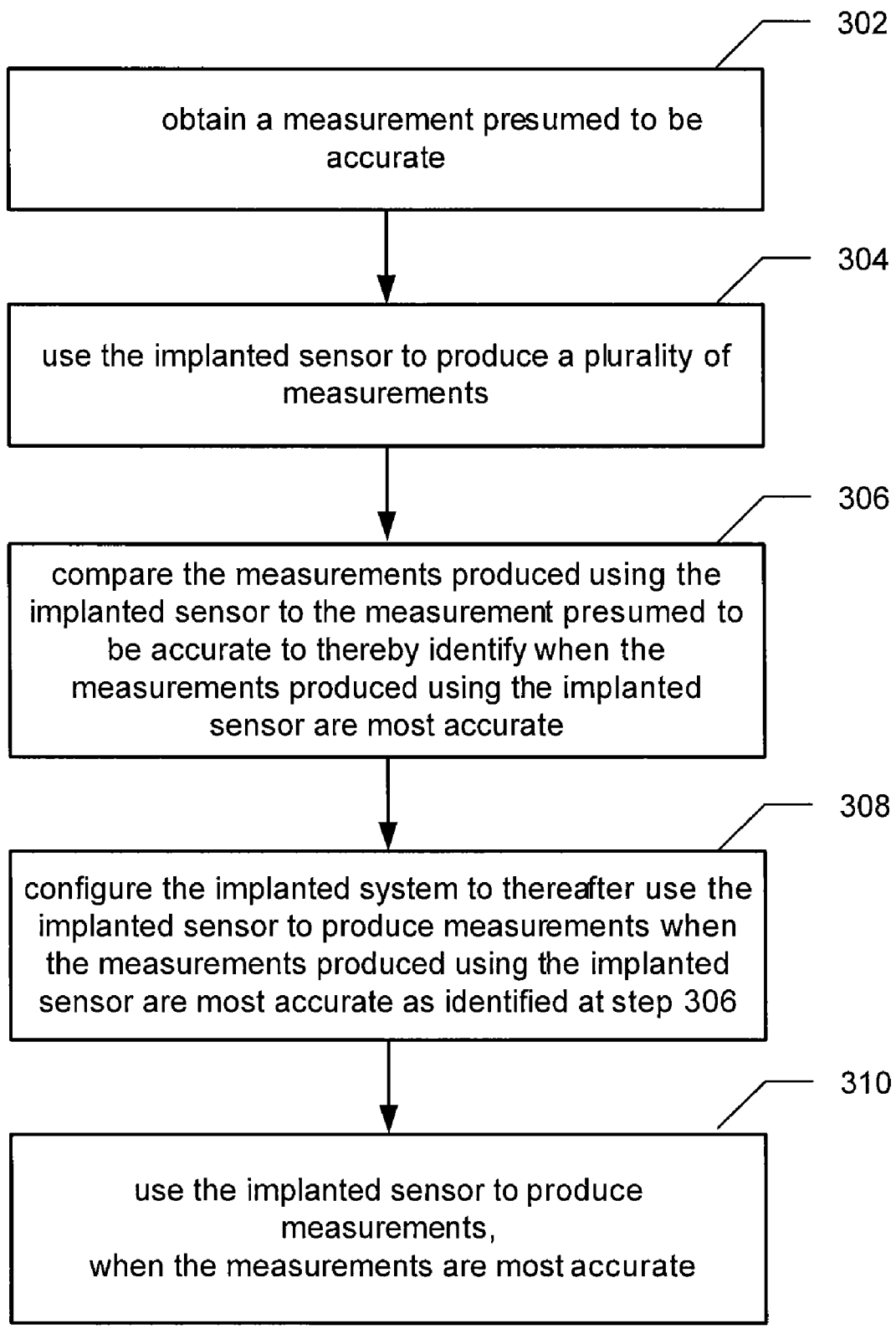
FIG. 3A is a high level flow diagram that is used to explain embodiments of the present invention used to increase the accuracy of measurements produced using an implanted sensor, where the measurements produced using the implanted sensor are affected by cycles of a cyclical body function.
Figure 3B:
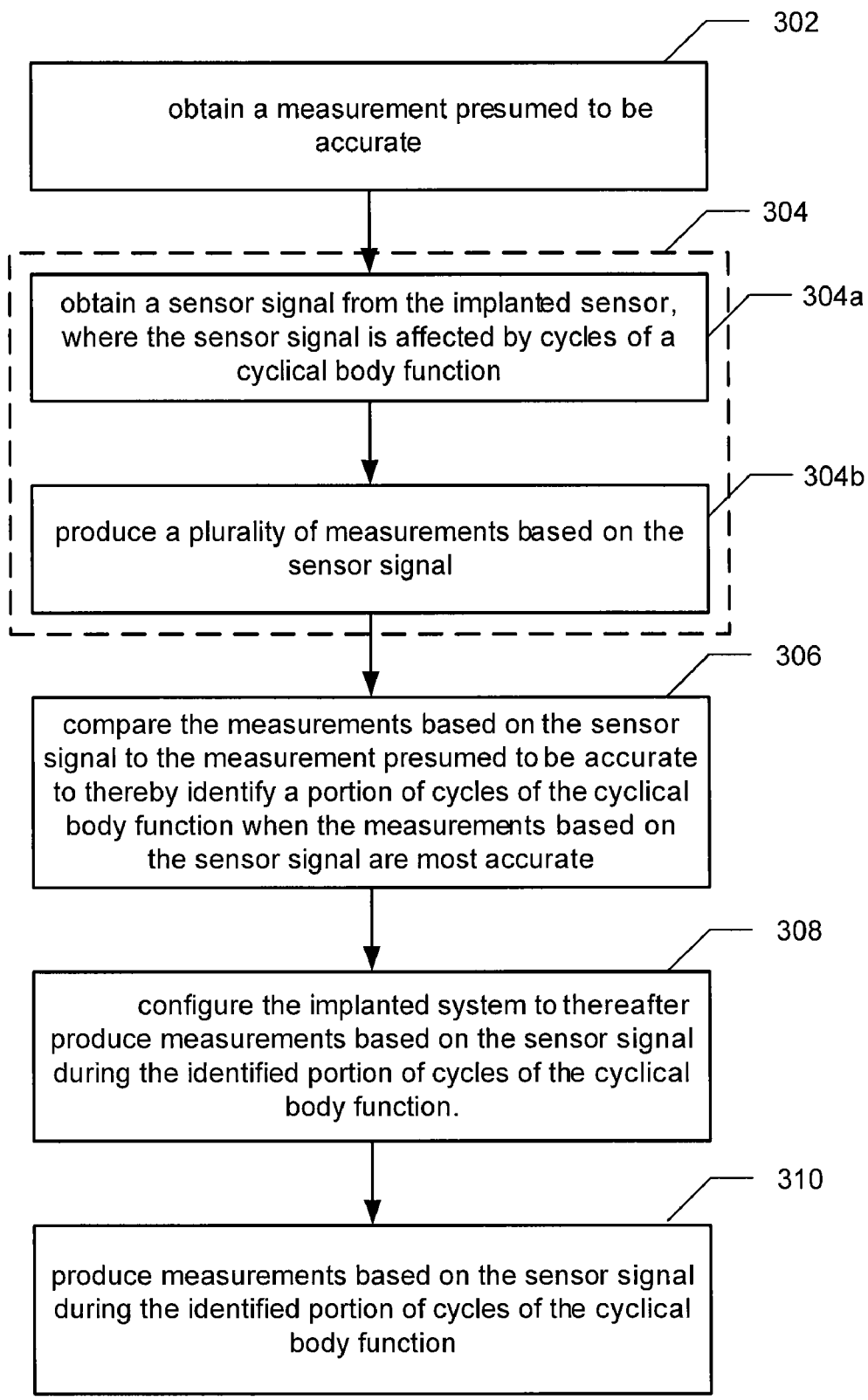
FIG. 3B is a high level flow diagram that is used to explain additional details of some of the steps of FIG. 3A, in accordance with specific embodiments of the present invention.

Specific embodiments of the present invention, which will now be summarized with reference to the high level flow diagrams of FIGS. 3A and 3B, take into account the above described phenomenon. More specifically, in accordance with specific embodiments of the present invention, the accuracy of measurements produced using an implanted sensor is increased, where the measurements produced using the implanted sensor are affected by cycles of a cyclical body function (e.g., heart beat and/or respiration).

Referring to FIG. 3A, at a step 302, one or more measurement presumed to be accurate is obtained. This can include, for example, obtaining an accurate measurement of venous oxygen saturation (SvO2) from a blood sample using a hemoximeter, or the like. Additionally, or alternatively, this can include obtaining an accurate measurement of hematocrit from a blood sample using a hematocrit centrifuge, where the blood sample is spun until red blood cells separate from the plasma, enabling a determination of what percentage of the total volume is red blood cells. These are just a few examples, which are not meant to be limiting. If alternative sensors are used, then the type of measurement obtained at step 302 can obviously be different. For example, if the accuracy of an implanted glucose sensor is to be improved, then step 302 can include obtaining an accurate measure of glucose from a blood sample. Increasing the accuracy of other hemodynamic measures, and more generally, other physiologic measures, are also within the scope of the present invention.

At a step 304, the implanted sensor is used to produce a plurality of measurements, of the same physiologic property for which a presumed accurate measurement is obtained at step 302. This can include, for example, using an implanted optical sensor to obtain measurements of venous oxygen saturation (SvO2) and/or hematocrit. At a step 306, measurements produced using the implanted sensor are compared to the measurement presumed to be accurate, to thereby identify when the measurements produced using the implanted sensor are most accurate. At a step 308, the implanted system is configured to thereafter use the implanted sensor to produce measurements when the measurements produced using the implanted sensor are most accurate as identified at step 306. Thereafter, as indicated at step 310, the implanted sensor is used to produce measurements, when the measurements are most accurate.

Step 308 can include, e.g., programming the implanted system to only sample the sensor signal during the portion of the sensor signal when the sensor signal is accurate, which in addition to increasing accuracy, would also reduce power consumption because sampling only needs to take place periodically, and less or no filtering will be required. Depending on the implementation, the implanted system can be programmed to produce as few as one sample per cycle of the cyclical body function. Alternatively, a plurality of samples can be produced during the portion of the signal that is most accurate, and the plurality of samples can be combined (e.g., averaged). Such programming of the implanted device, can be preformed using an external programmer, an example of which is discussed below.

Alternatively, the implanted system can be configured to sample the entire sensor signal (e.g., in accordance with a sample rate), but only those samples that are produced during the portion of the sensor signal when the sensor signal is accurate, are used for producing measurements. In other words, step 308 can include programming the implanted system to produce measurement using only the samples that are produced during the portion of the sensor signal when the sensor signal is accurate.

In still another embodiment, step 308 can include configuring the implanted system to power the implanted sensor only when the sensor will produce accurate measurements. For example, an optical SvO2 sensor may only power its light sources, when measurements of scattered light detected by the sensor's light detector(s) will be accurate.

FIG. 3B will now be used to explain how specific steps of FIG. 3A, can be implemented in accordance with specific embodiments of the present invention. Referring to FIG. 3B, step 304 is shown as including steps 304a and 304b. At step 304a, a sensor signal is obtained from the implanted sensor, where the sensor signal is affected by cycles of a cyclical body function. The cycles of a cyclical body function that affect the sensor signal can be, e.g., cardiac cycles of a patient's heart beat and/or respiratory cycles of a patient's respiration (i.e., breathing). At step 304b, measurements are produced based on the sensor signal. For example, if the implanted sensor is an optical SvO2 sensor, measurements of oxygen saturation and/or hematocrit can be produced based on the sensor signal.

Here, at step 306, measurements based on the sensor signal (e.g., from an implanted optical sensor) are compared to the measurement(s) presumed to be accurate (e.g., from a hemoximeter), to thereby identify a portion of cycles of the cyclical body function when the measurements based on the sensor signal are most accurate. This can include identifying the portion of cardiac cycles, when the measurements based on the sensor signal are most accurate, relative to a detectable cardiac event, such as, but not limited to, an intrinsic or paced ventricular event (e.g., detected as an R-wave). More specifically, at step 306 there can be a determination of how many milliseconds after detected R-waves (indicative of ventricular depolarization) the measurements based on the sensor signal are most accurate. For the examples of FIGS. 1A and 1B, the measurements of SvO2 and hematocrit based on the implanted optical sensor signal are most accurate from about 200 msec-300 msec after detected R-waves. Alternatively, at step 306, there can be a determination of at what percentage of cyclical cardiac intervals (e.g., R-R intervals) the measurements based on the sensor signal are most accurate. For the examples of FIGS. 1A and 1B, the measurements of SvO2 and hematocrit are most accurate during the portion of the sensor signal that corresponds to the last 50% of the R-R intervals, and more specifically, from about 60%-95% of the R-R intervals.

Where an EGM or ECG waveform is available, R-waves can be easily detected using well known detection schemes, which can be as simple as identifying maximum peaks in an EGM or ECG waveform, or can be much more complex. Other features, such as P-waves, indicative of cardiac events can also be detected from an EGM or ECG, and used as a reference point for determining when measurements using an implanted sensor are most accurate. However, if a separate EGM or ECG waveform is not available, the sensor signal itself can be used to identify the portion of cycles of a cyclical body function when the measurements based on the sensor signal are most accurate. This can be done by determining where in the sensor signal the measurements are most accurate, such as at the minimum, the maximum, or a certain time after such a signal feature of the signal. For example, the slope of a sensor signal can be found by taking a derivative. The slope can then be used to identify when the measurements based on the sensor signal are most accurate. Referring again to FIGS. 1A and 1B, the derivative would show a large positive slope at the R-wave, followed by a period of small slopes, followed by a large negative slope, followed by a period of relatively zero slope (shown at 112 and 132), which in this case is when the measurements based on the sensor signal are most accurate. For example, an algorithm can specify that samples of the sensor signal should only be taken after seeing a large negative slope, where the slope of the signal is relatively zero for at least a certain period of time, or at the minimum of the signal.

As mentioned above, the sensor signal can be affected by respiratory cycles of respiration. Thus, step 306 can include identifying the portion of respiratory cycles, when the measurements based on the sensor signal are most accurate, relative to a detectable respiratory event. Detectable respiratory events can be, e.g., inhalation and exhalation, which show up as minimums and maximums points of a respiratory waveform. More specifically, at step 306 there can be a determination of how many milliseconds after a minimum point (or maximum point) of a respiratory waveform the measurements based on the sensor signal are most accurate. Alternatively, at step 306, there can be a determination of at what percentage of a respiratory cycle (starting with a minimum or maximum point) the measurements based on the sensor signal are most accurate. A respiratory event can be defined in terms of a portion of the respiration waveform, and the most accurate measurements can occur at (or a determined delay after) the minimum, maximum, or midpoint of the respiration waveform. If a number of cardiac cycles occurs in each respiration cycle, there can be a determination of at which cardiac cycle number, the most accurate measurements occur. This could be defined as cycle number after a maximum or minimum point of a respiration waveform, or as a function of heart rate, since a change in heart rate would change the number of cardiac cycles within each respiratory cycle.

A separate respiration waveform from another sensor can be used to identify the portion of respiratory cycles, when the measurements based on a sensor signal are most accurate. If a separate waveform from a separate sensor is not available, the sensor's own signal can be low-pass filtered to create a low frequency signal indicative of respiration, and this low-pass filtered signal can be used to identify the portion of respiratory cycles, when the measurements based on a sensor signal are most accurate. This would introduce a delay to the output of the sensor, since the system would have to wait until at least an entire respiration wave has been recorded.

Where the sensor signal is affected by both cardiac cycles of heart beat and respiratory cycles of respiration, step 306 can include identifying when the measurements based on the sensor signal are most accurate relative to both detectable cardiac and respiratory events. Such identifying can be relative to separate cardiac and respiratory signals and/or relative to features of the sensor signal itself, which may or may not be filtered.

At step 308, the implanted system is configured (e.g., programmed) to thereafter produce measurements based on a portion of the sensor signal that corresponds to the identified portion of cycles of the cyclical body function. This can include, e.g., configuring the implanted system to only sample the portion of the sensor signal that corresponds to the identified portion of cardiac and/or respiratory cycles when the measurements based on the sensor signal are most accurate. Alternatively, this can include configuring the implanted system to sample the entire sensor signal (e.g., in accordance with a sample rate), but only use those samples that are produced during the identified portion of cardiac and/or respiratory cycles to produce measurements. In another embodiment, this can include configuring the implanted system to power the implanted sensor (or portion thereof) only during the identified portion of cardiac and/or respiratory cycles.

In accordance with specific embodiments of the present invention, there can be a determination of when measurements are most accurate for different cycle rates (e.g., heart rates and/or respiration rates), and the measurements can be taken at the same time/location of cycles regardless of cycle rate. More specifically, step 306 can be performed for a plurality of different cycle rates (e.g., heart rates and/or respiration rates), and step 308 can include identifying the portion of a cycle of the cyclical body function when the measurements based on the sensor signal are most accurate for the plurality of cycle rates. The different cycle rates used for calibration can be achieved by pacing or exercise, which decrease R-R intervals and reduce the window in which the measurements (e.g., SvO2 measurements) based on a sensor signal are most accurate. For example, at low heart rates, SvO2 measurements may be most accurate if based on the portion of the sensor signal that corresponds to the last 50% of R-R intervals (as shown in FIGS. 1A and 1B); and at high heart rates, SvO2 measurements might only be accurate if based on the portion of the sensor signal that corresponds to the last 20% of the R-R interval. In this case, an implantable device can be configured to produce measurements based on only the last 20% of the R-R interval, which would work in both of the above cases (i.e., at low and high heart rates).

Alternatively, if there is no overlap of where measurements based on the sensor signal are accurate for both low and high heart rates (e.g., if at high heart rates measurements based on the sensor signal are most accurate if based on the portion of the sensor signal that corresponds to the first 10% of the R-R interval), then the implantable device can be configured such that it adjusts with the current heart rate. In this case, several other heart rates could be tested. For example, there could be a threshold heart rate, and the portion of the sensor signal sampled to produce measurement of SvO2 could be different if heart rate is below the threshold or above the threshold. Multiple thresholds can be used to define further heart rate ranges, for each of which there can be an identification of when measurements using the sensor signal are most accurate.

A similar test could be performed with respiration, e.g., by changing the setting of a respirator, or if a patient is conscious he/she could be asked to perform shallow or deep breathing or to exercise. The sensor could then choose a setting that works for multiple ranges of respiration and depth, or have adjustable settings depending on the respiration rate and depth.

More generally, there can be a determination of when measurements are most accurate for each of a plurality of different cycle rates, and the measurements can be taken at a different time/location of the cycles, depending on the cycle rate. This can be accomplished by performing step 304 for a plurality of different cycle rates (e.g., heart rates and/or respiration rates), and step 306 can include identifying, for each of the different cycle rates, the portion of a cycle of the cyclical body function when the measurements based on the sensor signal are most accurate. Step 308 can include configuring the implanted system to thereafter produce measurements based on the sensor signal during the identified portion of a cycle of the cyclical body function, wherein the identified portion of the cycle is dependent upon the cycle rate. Similarly, step 310 can include producing measurements based on a portion of the sensor signal that corresponds to the identified portion of cycles of the cyclical body function, wherein the identified portion of the cycle is dependent upon the cycle rate.

In accordance with specific embodiments, accuracy can further be increased by determining an offset between the measurements based on the sensor signal obtained at step 304 and the measurement presumed to be accurate obtained at step 302. Accordingly, step 308 can include configuring the implantable system to adjust the measurements, produced based on the identified portion of the cycles of the cyclical body function, using the determined offset. For example, if an average of a plurality of samples of a sensor signal are taken during a specific portion of R-R intervals to produce each measurement of SvO2, then such averages should be compared to the measurement presumed to be accurate, to determine the offset. In specific embodiments, the offset could be determined at implant, and could subsequently be subtracted from or added to the SvO2 measurements based on a sensor signal of an implanted optical SvO2 sensor. The offset can be fixed or variable. If the offset is fixed, it can be expressed as an absolute value or percentage. If the offset is dynamic, it can be expressed, e.g., as a percentage change. For example, in the latter case, the offset at high SvO2 levels might be higher than the offset at the low SvO2 levels.

It would be apparent to one of ordinary skill in the relevant art that some of the steps discussed with reference to FIGS. 3A and 3B need not be performed in the exact order described. For example, step 304 can occur before or concurrent with step 302. However, it would also be apparent to one of ordinary skill in the relevant art that some of the steps should be performed before others. This is because certain steps use the results of other steps. The point is, the order of the steps is only important where a step uses results of another step. Accordingly, one of ordinary skill in the relevant art would appreciate that embodiments of the present invention should not be limited to the exact orders shown in FIGS. 3A and 3B. Additionally, one of ordinary skill in the relevant art would appreciate that embodiments of the present invention can be implemented using subgroups of the steps that are shown in FIGS. 3A and 3B.

In further embodiments of the presenting invention, the accuracy of a sensor is increased by recording characteristics of the sensor signal during "extreme" conditions, such as deep and/or shallow breathing, elevated heart rate on a bike/treadmill, walking, rapid pacing, base rate pacing (slightly above intrinsic rate), resting, laying down, etc. This information could be used in several ways. In certain embodiments, an algorithm can take advantage of the fact that during these conditions, un-wanted artifacts or patterns (e.g., respiration induced noise, constant motion induced noise, etc) in the signal will be the highest/lowest and may be used to calibrate the sensor signal on a continuous basis or at a patient follow-up. Assuming other conditions remain unchanged, patterns of an SvO2/un-wanted artifact recording may be similar at a given condition, irrespective of timing. One way of utilizing the artifacts is to store characteristic of the artifacts in the device and later compare a collected signal to the stored characteristics (e.g., template waveforms). For example, templates can be saved, or information about peak amplitudes or other characteristics can be saved. If similar artifacts are seen later, the implanted device will know that they correspond to extreme conditions and can disregard the sensor signal, or can filter the sensor signal accordingly, or adjust an extent of filtering. Alternatively or additionally, such artifacts can also be used as a substitute for an activity sensor, by finding times of heightened activity. Another way of utilizing the artifacts is using lack of artifacts to determine a time of rest. This can be useful for safely collecting a noise-free sensor signal or for periodic updating of certain parameters (e.g. morphology templates, EGM timing).

Exemplary Cardiac Stimulation Device

As described above, embodiments of the present invention can be used to improve the accuracy of implantable sensors. Such sensor can be located within the housing of an implantable cardiac stimulation device, attached to the housing of such a device, attached by a lead to such a device, or wirelessly in communication with such a device. Accordingly, for completeness an exemplary cardiac stimulation device is described below with reference to FIGS. 4A and 4B.

Figure 4A:
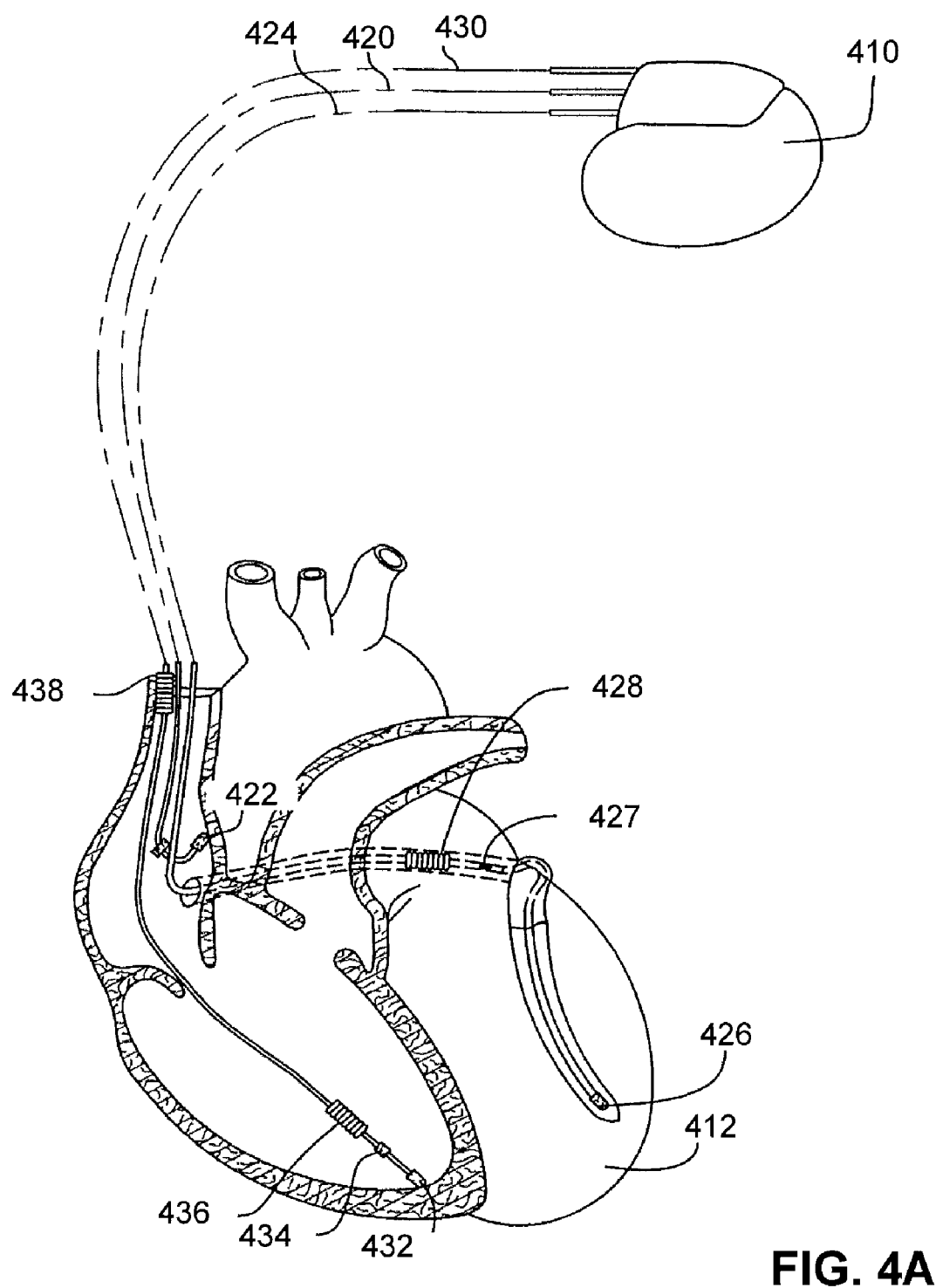
FIG. 4A illustrates an exemplary implantable cardiac stimulation device in electrical communication with a patient's heart by way of three leads, which are suitable for delivering multi-chamber stimulation and shock therapy.

Referring to FIG. 4A, an exemplary implantable cardiac stimulation device 410 is shown as being in electrical communication with a patient's heart 412 by way of three leads, 420, 424 and 430, suitable for delivering multi-chamber stimulation and shock therapy. Certain features of the various embodiments of the present invention can be implemented by an implantable device that is similar to device 410, or by an implantable device that includes more or less functionality than device 410.

To sense atrial cardiac signals and to provide right atrial chamber stimulation therapy, the stimulation device 410 is coupled to an implantable right atrial lead 420 having at least an atrial tip electrode 422, which typically is implanted in the patient's right atrial appendage.

To sense left atrial and ventricular cardiac signals and to provide left-chamber pacing therapy, the stimulation device 410 is coupled to a "coronary sinus" lead 424 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428.

The stimulation device 410 is also shown in electrical communication with the patient's heart 412 by way of an implantable right ventricular lead 430 having, in this embodiment, a right ventricular tip electrode 432, a right ventricular ring electrode 434, a right ventricular (RV) coil electrode 436, and an SVC coil electrode 438. Typically, the right ventricular lead 430 is transvenously inserted into the heart 412 so as to place the right ventricular tip electrode 432 in the right ventricular apex so that the RV coil electrode 436 will be positioned in the right ventricle and the SVC coil electrode 438 will be positioned in the superior vena cava. Accordingly, the right ventricular lead 430 is capable of receiving cardiac signals and delivering stimulation in the form of pacing and shock therapy to the right ventricle.

Figure 4B:
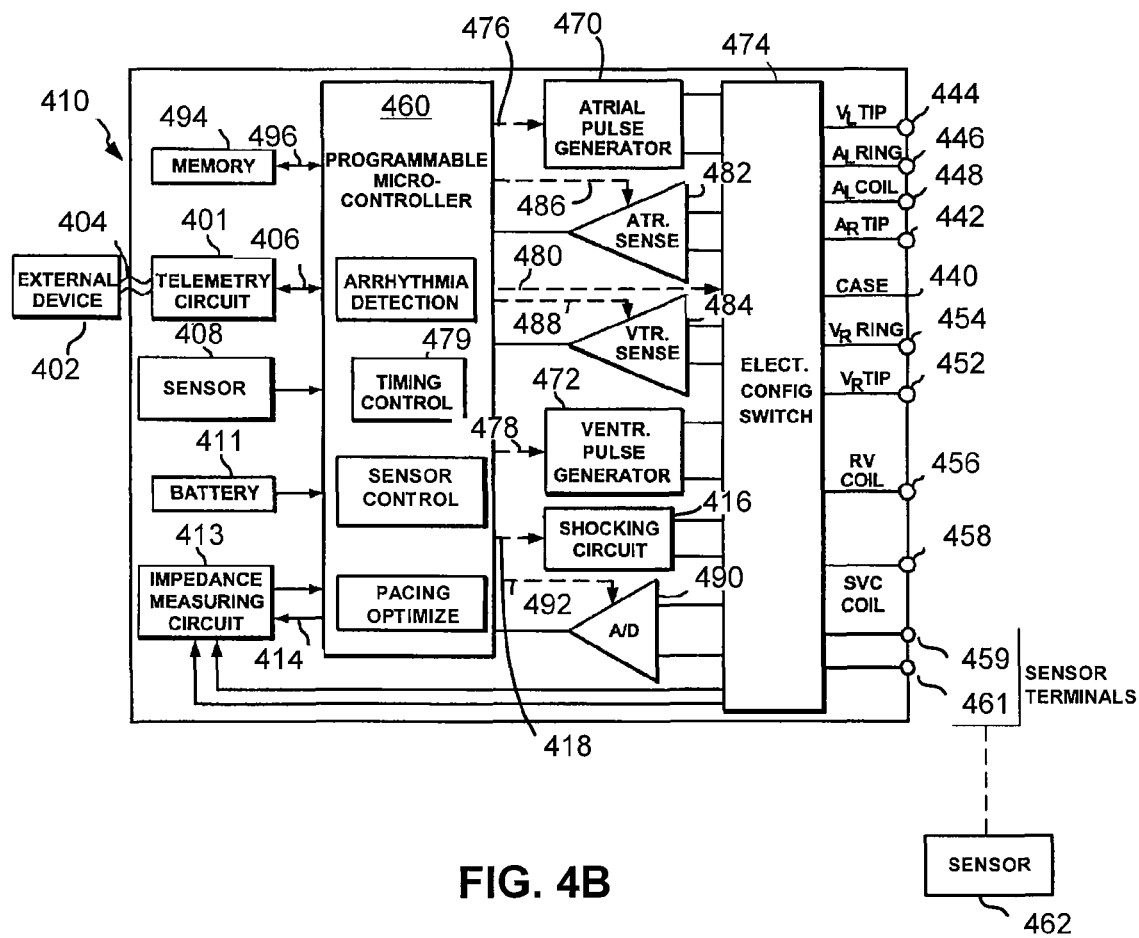
FIG. 4B is a simplified block diagram of the multi-chamber implantable stimulation device of FIG. 4A.

As illustrated in FIG. 4B, a simplified block diagram is shown of the multi-chamber implantable stimulation device 410, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 440 for the stimulation device 410, shown schematically in FIG. 4B, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 444, 446, 448, 452, 454, 456, and 458 (shown schematically and, for convenience, the names of the electrodes to which they are connected are shown next to the terminals).

As such, to achieve right atrial sensing and pacing, the connector includes at least a right atrial tip terminal (AR TIP) 442 adapted for connection to the atrial tip electrode 422.

To achieve left chamber sensing, pacing and shocking, the connector includes at least a left ventricular tip terminal (VL TIP) 444, a left atrial ring terminal (AL RING) 446, and a left atrial shocking terminal (AL COIL) 448, which are adapted for connection to the left ventricular tip electrode 426, the left atrial ring electrode 427, and the left atrial coil electrode 428, respectively.

To support right chamber sensing, pacing and shocking, the connector further includes a right ventricular tip terminal (VR TIP) 452, a right ventricular ring terminal (VR RING) 454, a right ventricular shocking terminal (RV COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

The connector is also shown as including sensor terminals 459 and 461 which can be configured for connection to the wires a sensor module located on or within a lead.

At the core of the stimulation device 410 is a programmable microcontroller 460 which controls the various modes of stimulation therapy, including pacing optimization and anti-arrhythmia therapy. Such a microcontroller can include, e.g., one or more processor.

A sensor 462 that is sensitive to changes in cyclical body functions (e.g., respiration and/or heart beat), can be attached to the implantable device 410 by one or more lead connected to terminals 459 and/or 461 to thereby provide an analog sensor signal to the implantable device. Such a sensor can be attached to a lead or located within a lead. Switch 474 can provide such a signal to an analog-to-digital (A/D) converter 490 that converts the signal to a digital format (e.g., into sample data) understood by the microcontroller 460. It is also possible that a dedicated A/D converter be provided within the implantable device 410 for the purpose of digitizing a signal received from the sensor 462 which is sensitive to changes in cyclical body functions, such as respiration and heart beat. If the sensor 462 provides a digital signal to the implantable device 410, then such a signal may be provided directly to the microcontroller 410. Using techniques described above, the microcontroller 410 can be configured to use the implanted sensor 462 to produce measurements when the measurements will be most accurate.

A sensor 408 that is sensitive to changes in cyclical body functions (e.g., respiration and/or heart beat) can be located within the housing 440, or within a further housing (not shown) attached to the housing 440. Where the sensor 408 is an optical oxygen saturation and/or hematocrit sensor, the housing containing the sensor may include one or more window to allow for light transmission/reflection, as will be understood from the various applications and patents incorporated herein by reference above.

The sensor(s) 408 and/or 462 can be an oxygen saturation sensor and/or hematocrit sensor. Alternatively, or additionally, the sensor 408 and/or 462 can be an impedance sensor, pressure sensor, other protein sensors, or the like. These are just a few exemplary implantable sensors that may produce a sensor signal that is affected by cycles of a cyclical body function. Embodiments of the present invention can also be used with other sensors that measure physiologic properties other than those just mentioned. Accordingly, sensor(s) 408 and/or 462 can be other types of sensor.

In specific embodiments, the microcontroller 460 can determine measures of blood oxygen saturation, hematocrit, glucose, or some other physiologic property based on the signal it receives from a sensor(s) (e.g., 408 and/or 462), which can be located within the housing 440, or attached to or within a sensor lead 420, 424 and/or 430. Such measures of can be used, e.g., for pacing optimization, disease monitoring, and the like. Additionally or alternatively, the measures of a physiologic property can be stored in memory 494 for later transmission to an external device 402 using the telemetry circuit 401.

As is well known in the art, the microcontroller 460 can include one or more microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 460 includes the ability to analyze signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing, control and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inteRRelationship, see U.S. Pat. No. 4,788,980 (Mann et. al.). The '052, '555, '298 and '980 patents are incorporated herein by reference.

As shown in FIG. 4B, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. The switch 474 can also be used to connect wires from a sensor to appropriate I/O circuits.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables the device 410 to deal effectively with the difficult problem of sensing the low amplitude signal characteristics of atrial or ventricular signals.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 410 utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 402. The data acquisition system 490 is coupled to the right atrial lead 420, the coronary sinus lead 424, and the right ventricular lead 430 through the switch 474 to sample cardiac signals across any pair of desired electrodes.

The data acquisition system 490 can be coupled to the microcontroller 460, or other detection circuitry, for detecting an evoked response from the heart 412 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 460 is further coupled to a memory 494 by a suitable data/address bus 496, wherein the programmable operating parameters used by the microcontroller 460 can be stored and modified, as required, in order to customize the operation of the stimulation device 410 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 412 within each respective tier of therapy.

Data acquired by the data acquisition system 490 (and optionally stored) can be used for subsequent analysis to guide the programming of the device and/or to monitor oxygen saturation, appropriately adjust pacing interval parameters, select optimum pacing intervals, and/or select appropriate anti-arrhythmia therapy. In accordance with specific embodiments, template information can be stored in memory 494. Additionally, threshold(s) and bin definitions can be stored in memory 494.

The operating parameters of the implantable device 410 may be non-invasively programmed into the memory 494 through a telemetry circuit 401 in telemetric communication with the external device 402, such as a programmer, transtelephonic transceiver, or a diagnostic system analyzer. The telemetry circuit 401 is activated by the microcontroller by a control signal 406. The telemetry circuit 401 advantageously allows intracardiac electrograms, oxygen saturation information and status information relating to the operation of the device 410 (as contained in the microcontroller 460 or memory 494) to be sent to an external device 402 through an established communication link 404. An external programmer, or other external device, can be used to assist with the configuring of an implanted system, in accordance with embodiments of the present invention. For example, an external programmer or the like can be use to perform at least a portion of steps 306 and/or 308, or to control the performance of such steps.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

The stimulation device 410 additionally includes a battery 411 which provides operating power to all of the circuits shown in FIG. 4B. For the stimulation device 410, which employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected. The battery 411 can also power the sensor that is sensitive to changes in cyclical body functions. A separate battery may alternatively be used.

The stimulation device 410 can further include a magnet detection circuitry (not shown), coupled to the microcontroller 460. It is the purpose of the magnet detection circuitry to detect when a magnet is placed over the stimulation device 410, which magnet may be used by a clinician to perform various test functions of the stimulation device 410 and/or to signal the microcontroller 460 that the external programmer 402 is in place to receive or transmit data to the microcontroller 460 through the telemetry circuits 401.

As further shown in FIG. 4B, the device 410 is shown as having an impedance measuring circuit 413 which is enabled by the microcontroller 460 via a control signal 414. The known uses for an impedance measuring circuit 413 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 413 is advantageously coupled to the switch 474 so that any desired electrode may be used. In addition, to facilitate the measurement of peripheral tissue edema, extra electrodes can be added to the device housing, thereby limiting the test electric field to the peripheral tissue.

In the case where the stimulation device 410 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (4 to 40 Joules), as controlled by the microcontroller 460. Such shocking pulses are applied to the patient's heart 412 through at least two shocking electrodes, and as shown in this embodiment, selected from the left atrial coil electrode 428, the RV coil electrode 436, and/or the SVC coil electrode 438. As noted above, the housing 440 may act as an active electrode in combination with the RV electrode 436, or as part of a split electrical vector using the SVC coil electrode 438 or the left atrial coil electrode 428 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of ventricular fibrillation. Accordingly, the microcontroller 460 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Features of the present invention can be performed at or shortly after implant of an implantable system that includes an implantable sensor that is sensitive to changes in cyclical body functions. Additionally, or alternatively, embodiments of the present invention can be used at later times after implantation to essentially recalibrate the system, just in case the sensor has moved, tissue has grown over the sensor and/or other changes have occurred. At any of the above times, an external programmer or other external device can transmit the measurement presumed to be accurate (obtained at step 302) to the implanted system, and the implanted system can perform the other steps (e.g., steps 304-310). Alternatively, the implanted system can transmit measurements produced using an implanted sensor to an external device (e.g., external programmer), and the external device can perform certain steps (e.g., step 306) and control the performance of other steps (e.g., step 308).

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A method for increasing accuracy of measurements produced using an implanted sensor implanted within a patient, where the measurements produced using the implanted sensor are affected by cycles of a cyclical body function, the method comprising:
   (a) obtaining an accurate measurement of a physiologic property for the patient;
   (b) using the implanted sensor to produce a plurality of measurements of a same physiologic property as the physiologic property for which the accurate measurement is obtained at step (a);
   (c) comparing the measurements produced using the implanted sensor at step (b) to the accurate measurement obtained at step (a) to thereby identify when relative to the cyclical body function the measurements produced using the implanted sensor are most accurate; and
   (d) configuring the implanted system to thereafter use the implanted sensor to produce measurements of the same physiologic property when the measurements produced using the implanted sensor are most accurate as identified at step (c).

2. The method of claim 1, wherein:
   step (c) comprises comparing the measurements produced using the implanted sensor to the accurate measurement obtained at step (a) to thereby identify a portion of cycles of the cyclical body function when the measurements produced using the implanted sensor are most accurate; and step (d) comprises configuring the implanted system to thereafter use the implanted sensor to produce measurements during the identified portion of cycles of the cyclical body function.

3. The method of claim 2, wherein:

step (c) comprises identifying a portion of cardiac cycles, when the measurements produced using the implanted sensor are most accurate, relative to a detectable cardiac event as detected from a signal representative of cardiac activity.

4. The method of claim 2, wherein:

step (c) includes identifying a portion of cardiac cycles, when the measurements produced using the implanted sensor are most accurate, relative to a detectable feature of a sensor signal produced by the implanted sensor.

5. The method of claim 1, wherein:

step (b) comprises (b.1) obtaining a sensor signal from the implanted sensor; and (b.2) producing a plurality of measurements based on the sensor signal;

step (c) comprises comparing the measurements based on the sensor signal to the accurate measurement obtained at step (a) to thereby identify a portion of cycles of the cyclical body function when the measurements based on the sensor signal are most accurate; and step (d) comprises configuring the implanted system to thereafter produce measurements based on a portion of the sensor signal that corresponds to the identified portion of cycles of the cyclical body function.

6. The method of claim 5, wherein the cyclical body function is heart beat, and the cycles of the cyclical body function are cardiac cycles.

7. The method of claim 6, wherein:

step (d) including identifying the portion of cardiac cycles, when the measurements based on the sensor signal are most accurate, relative to a detectable cardiac event.

8. The method of claim 7, wherein in step (d) the identifying includes determining at what time interval after specific detected features of a signal indicative of cardiac activity the measurements based on the sensor signal are most accurate.

9. The method of claim 6, wherein in step (d) the identifying includes determining at what percentage of cyclical cardiac intervals the measurements based on the sensor signal are most accurate.

10. The method of claim 5, wherein the cyclical body function is respiration, and the cycles of the cyclical body function are respiratory cycles.

11. The method of claim 10, wherein:

step (d) including identifying the portion of respiratory cycles, when the measurements based on the sensor signal are most accurate, relative to a detectable respiratory event.

12. The method of claim 10, wherein:

step (d) including identifying the portion of respiratory cycles, when the measurements based on the sensor signal are most accurate, relative to a detectable feature of a low-pass filtered version of the sensor signal.

13. The method of claim 5, wherein:

the sensor signal is affected by both cardiac cycles of heart beat and respiratory cycles of respiration; and step (d) includes identifying when the measurements based on the sensor signal are most accurate relative to both detectable cardiac and respiratory events.

14. The method of claim 5, wherein the physiologic property comprises one of venous oxygen saturation, hematocrit and blood glucose concentration.

15. The method of claim 5, wherein:

step (b) is performed for a plurality of different cycle rates; and step (c) includes identifying the portion of cycles of the cyclical body function when the measurements based on the sensor signal are most accurate for the plurality of cycle rates.

16. The method of claim 5, wherein:

step (b) is performed for a plurality of different cycle rates;

step (c) includes identifying, for each of the different cycle rates, the portion of cycles of the cyclical body function when the measurements based on the sensor signal are most accurate; and step (d) includes configuring the implanted system to thereafter produce measurements based on the sensor signal during the identified portion of cycles of the cyclical body function, wherein the identified portion of the cycles is dependent upon the cycle rate.

17. The method of claim 5, further comprising:

determining an offset between the measurements based on the sensor signal produced at step (b) and the accurate measurement obtained at step (a); and configuring the implantable system to adjust the measurements, produced using the implanted sensor during the identified portion of the cycles of the cyclical body function, using the determined offset.

18. The method of claim 1, wherein step (c) includes identifying, a portion of cycles of the cyclical body function when the measurements produced using the implanted sensor are closest to the accurate measurement obtained at step (a).

19. A method for increasing accuracy of measurements based on a sensor signal obtained from an implanted sensor of an implanted system implanted within a patient, where the sensor signal is affected by cycles of a cyclical body function, the method comprising:

(a) obtaining an accurate measurement of a physiologic property for the patient;

(b) producing, based on the sensor signal, a plurality of measurements of the a same physiologic property as the physiologic property for which the accurate measurement is obtained at step (a);

(c) comparing the measurements based on the sensor signal to the accurate measurement to thereby identify a portion of cycles of the cyclical body function when the measurements based on the sensor signal are most accurate; and (d) producing measurements based on a portion of the sensor signal that corresponds to the identified portion of cycles of the cyclical body function.

20. The method of claim 19, wherein step (c) includes identifying, a portion of cycles of the cyclical body function when the measurements produced based on the sensor signal are closest to the accurate measurement obtained at step (a).

21. An implantable system, comprising:

an implantable sensor that can be used to produce measurements of a physiologic property, where the measurements are affected by cycles of a cyclical body function; and one or more processor configured to:

compare measurements produced using the implanted implantable sensor to a separate accurate measurement of a same physiologic property to thereby identify when relative to the cyclical body function the measurements produced using the implantable sensor are most accurate; and thereafter use the implantable sensor to produce measurements of the same physiologic property when the measurements produced using the implantable sensor are most accurate as identified.

22. The implantable system of claim 21, wherein:

the implantable sensor produces a sensor signal from which measurements of the same physiologic property can be made; and the one or more processor is configured to:

identify a portion of cycles of the cyclical body function when the measurements produced based on the sensor signal are most accurate; and thereafter use the implantable sensor to produce measurements based on a portion of the sensor signal that corresponds to the identified portion of cycles of the cyclical body function.

23. The implantable system of claim 22, further comprising:

a filter to low-pass filter the sensor signal to produce a low-pass filtered version of the sensor signal; and wherein the one or more processor is configured to identify the portion of respiratory cycles, when the measurements based on the sensor signal are most accurate, relative to a detectable feature of the low-pass filtered version of the sensor signal.

24. The implantable system of claim 22, wherein:

the sensor signal is affected by both cardiac cycles of heart beat and respiratory cycles of respiration; and the one or more processor is configured to identify when the measurements based on the sensor signal are most accurate relative to both detectable cardiac and respiratory events.

25. The implantable system of claim 22, wherein:

the one or more processor is also configured to:

determine an offset between the measurements based on the sensor signal and the accurate measurement; and adjust the measurements, produced based on the sensor signal, using the determined offset.

26. The implantable system of claim 22, wherein the one or more processor is configured to identify a portion of cardiac cycles, when the measurements produced using the implantable sensor are most accurate, relative to a detectable cardiac event as detected from a signal representative of cardiac activity.

27. The implantable system of claim 22, wherein the one or more processor is configured to identify a portion of cardiac cycles, when the measurements produced using the implantable sensor are most accurate, relative to a detectable feature of the sensor signal produced by the implantable sensor.

28. The implantable system of claim 22, wherein the one or more processor is configured to identify a portion of respiratory cycles, when measurements produced using the implantable sensor are most accurate, relative to a detectable respiratory event.

29. The implantable sensor of claim 21, wherein the one or more processor is configured to identify, a portion of cycles of the cyclical body function when the measurements produced based on the sensor signal are closest to the separate accurate measurement of the same physiologic property.

* * * * *